(12) United States Patent
Krauter et al.

(10) Patent No.: US 7,102,045 B2
(45) Date of Patent: Sep. 5, 2006

(54) METHOD FOR CARRYING OUT-CC-COUPLING REACTIONS

(75) Inventors: Jürgen Krauter, Dreieich (DE); Jörg Pietsch, Kälberauer Strasse (DE); Peter Panster, Rodenbach (DE); Klaus Köhler, Ismaning (DE); Roland Heidenreich, München (DE)

(73) Assignee: Degussa AG, Dusseldorf (DE)

( * ) Notice: Subject to any disclaimer, the term of this patent is extended or adjusted under 35 U.S.C. 154(b) by 232 days.

(21) Appl. No.: 10/363,237

(22) PCT Filed: Jul. 18, 2001

(86) PCT No.: PCT/EP01/08259

§ 371 (c)(1),
(2), (4) Date: Mar. 6, 2003

(87) PCT Pub. No.: WO02/20433

PCT Pub. Date: Mar. 14, 2002

(65) Prior Publication Data

US 2003/0181748 A1    Sep. 25, 2003

(51) Int. Cl.
C07C 2/08   (2006.01)
C07C 2/72   (2006.01)

(52) U.S. Cl. .................. 585/429; 585/425; 585/427
(58) Field of Classification Search .............. 560/264
See application file for complete search history.

(56) References Cited

FOREIGN PATENT DOCUMENTS

DE    42 36 103 A    4/1994
EP    0 509 426 A    10/1992

OTHER PUBLICATIONS

Marck et al, Tetrahedron Letters, (1994), vol.35 (20) pp. 3277-3280.*
Blaser et al, Supported palladium catalysts for fine chemicals synthesis, Journal of Molecular Catalysis A: Chemical vol. 173 (2001) 3-18.*
G. Marck, "Aryl couplings with heterogeneous palladium catalysts", Tetrahedron Letters, 1994, pp. 3277-3280, vol. 35, and No. 20.
M. Julia, "Etude de la condensation de chlorures aromatiques avec les oléfines catalysée par le palladium", Bulletin De La Societe Chimique De France, 1973, pp. 2791-2794 and No. 9-10.

* cited by examiner

*Primary Examiner*—Brian Davis
(74) *Attorney, Agent, or Firm*—Venable LLP; Thomas G. Wiseman (57) ABSTRACT

The invention relates to a method for carrying out CC-coupling reactions, in particular a Heck and Suzuki reaction, in the presence of supported palladium as the catalyst and a base in a monophase or multiphase solvent mixture. According to said method, palladium detaches itself from the support in a characteristic manner, is redeposited after the reaction and the quantity of palladium not deposited after the reaction is significantly lower than 5000 ppm, in relation to the palladium used.

34 Claims, 4 Drawing Sheets

Fresh (left) and used (right) catalyst; TEM photograph 1:200,000

Figure 1

Fresh (left) and used (right) catalyst; TEM photograph 1:400,000

METHOD FOR CARRYING OUT-CC-COUPLING REACTIONS

RELATED APPLICATIONS

This application is a national stage filing under 35 U.S.C. 371 based on international application No. PCT/EP01/08259 filed on Jul. 18, 2001 which international application claims priority to European Patent Application No. 00119534.6 filed Sep. 7, 2000.

TECHNICAL FIELD

The invention relates to a process for carrying out CC coupling reactions, such as the Heck reaction and variants, Suzuki coupling, allyl substitution, Sonogashira coupling (alkine coupling) and Kumada coupling, employing heterogeneous noble metal powder catalysts.

BACKGROUND ART

Palladium-catalysed CC coupling reactions (for example Suzuki coupling, allyl substitution, the Heck reaction) play an important role in preparative organic chemistry. In particular, the toleration of many functional groups, which makes an expensive protective group technique superfluous, make CC coupling reactions particularly attractive for fine chemistry and pharmaceutical chemistry.

Homogeneous catalysts for CC coupling reactions are known. On a production scale, with these catalysts it is essential to remove the palladium from the reaction solution in a further process step. Since in most cases the noble metal palladium is used as catalytically active metal, it must be separated off as quantitatively as possible. On the one hand, the expensive noble metal can be recovered in this way, and on the other hand contamination of the product with noble metal is avoided.

Numerous disadvantages are associated with the use of homogeneous catalysts for CC coupling reactions according to the prior art. After the reaction has taken place, the noble metal must be separated off from the reaction mixture in an expensive manner, which complicates the preparation process. Homogeneous catalysts are in general composed of the noble metal and ligands which are in a particular stoichiometric ratio with respect to one another. These ligands also make purification of the product expensive. Inert gas conditions (nitrogen or argon atmosphere) are very often required, so that the catalyst is not destroyed before or during the reaction.

It is known that CC coupling reactions can be carried out with heterogeneous catalysts. Augustine (R. L. Augustine, S. T. O'Leary, *J. Mol. Catal.* 1995, 95, 277–285) describes, for example, the reaction of aromatic carboxylic acid chlorides with butyl vinyl ether to give 2-butoxyethenylbenzenes. Eisenstadt (EP 509 426) describes the preparation of UV absorbers with the aid of heterogeneous Pd/C catalysts.

Numerous problems are also linked with the use of heterogeneous catalysts for CC coupling reactions according to the prior art. When halogenoaromatics are employed in, for example, the Heck reaction, an undesirable dehalogenation is often observed.

In direct comparison between homogeneous and heterogeneous catalyst systems, the heterogeneous systems show lower activities than the homogeneous systems.

A very important aspect, which is often not considered in the literature, is the detachment of the noble metal from the support during and/or after the reaction. Where detachment of the noble metal from the support has been investigated at all, this is often so high that contamination of the product takes place. According to the current prior art, it is very expensive or as a rule even impossible to separate off the noble metal completely.

DISCLOSURE OF THE INVENTION

The object of the present invention is to provide a process for the catalytic preparation of CC coupling products which does not have the disadvantages described above.

The invention provides a process for carrying out CC coupling reactions, such as Heck reactions and variants, Suzuki coupling, allyl substitution, Sonogashira coupling (alkyne coupling) and Kamada coupling, in particular Heck reactions and variants thereof and the Suzuki reaction, and for separating off the Pd employed from the mother liquor, which is characterized in that a supported palladium catalyst is employed. In one embodiment of the invention, it is possible to employ no ligands with the catalyst.

According to the invention, a substituted aromatic or a halogen-substituted olefin can be reacted with an olefin (Heck reaction) or with an arylboron acid (Suzuki reaction) in the presence of a heterogeneous pulverulent palladium catalyst and in the presence of a base in an organic or two-phase solvent mixture at temperatures of between 60 and 220° C., preferably 80 and 180° C., particularly preferably 120 and 160° C. (Heck reaction) or between 40 and 180° C., preferably 60 and 160° C., particularly preferably 80 and 120° C. (Suzuki reaction).

In carrying out the process according to the invention, the heterogeneous palladium catalyst can be employed as a water-moist or dry powder or as a water-moist or dry powder which has been pressed to shaped bodies. The water content of the dry catalyst can be between 0.5 and 3.5 wt. %. The water-moist powder form, i.e. a water content of 30 to 70 wt. %, preferably a water content of 40 to 60 wt. %, particularly preferably a water content of 45 to 55 wt. %, can preferably be employed.

The heterogeneous Pd catalyst can be prepared by known methods, such as are described, for example, by Pearlman (W. M. Pearlman, *Tetrahedron Lett.* 1967, 17, 1663–1664). Furthermore, the catalysts can be obtained from Degussa-Hüls AG as commercially obtainable catalysts, for example under the following trade name E 105 O/W 5% Pd (the noble metal powder catalyst technology brochures of Degussa-Hüls AG).

The catalysts can be characterized in that after the wet chemistry preparation they are not treated in a separate conditioning step (for example with nitrogen or forming gas). The activities of the catalysts drop considerably by thermal after-treatment, and an improvement in the recovery of the noble metal is not thereby achieved.

The catalysts can be characterized in that they have a noble metal loading of 0.1 to 30 wt. % of Pd, and preferably contain 1 to 10 wt. %, particularly preferably 5 wt. %.

The catalysts can be characterized in that they have no sharp shell-like distribution of the noble metal crystallites in the supported catalyst grain. The penetration depth of the Pd crystallites can be between 50 nm and homogeneous distribution, preferably >300 nm. A homogeneous distribution is particularly preferred.

The catalysts can be characterized in that the average noble metal dispersion is between 10 and 60%, preferably between 15 and 50%, particularly preferably between 20 and 40%. The dispersion is calculated from the CO chemisorption values by dividing the value measured by the maximum theoretically possible value for Pd (assuming a stoichiometric ratio of 1:1=Pd:CO).

The catalysts can be characterized in that they have a low degree of reduction (the degree of reduction is defined as the ratio of the amount of hydrogen measured to the hydrogen theoretically required for complete reduction of the total noble metal on the support) of between 0 and 50%, preferably between 0 and 40%, particularly preferably between 0 and 20%. The measurement is carried out with the aid of TPR (temperature-programmed reduction).

The catalysts can be characterized in that a support material based on carbon (for example active charcoal, wood charcoal, carbon black, graphite), preferably active charcoal, particularly preferably physically activated active charcoals, is used. The support material can be characterized in that it has a BET surface area of at least 800 m$^2$/g (according to ASTM D3663), a micropore volume of less than 0.4 ml/g (according to ASTM D4365), a mesopore volume of greater than 0.3 ml/g (according to ASTM D4641) and a macropore volume of greater than 0.3 ml/g (according to ASTM D4284).

The catalysts can be characterized in that during the reaction a characteristic detachment, depending on the base used and the solvent used, of the Pd introduced from the support and during and after the reaction redeposition of the Pd detached from the support on to the support occurs, which depends on the decisive parameters of conversion, temperature, substrate, base and solvent, where complete conversion, temperatures above 110° C., reducing bases, such as amines or formates, and nonpolar solvents are preferred, and in particular the deposition is particularly good in two-phase solvent mixtures of an organic solvent and water.

This can be demonstrated by suitable sampling during the reaction and Pd determinations. The detachment (min. 60° C.) and deposition (min. 120° C.) are characterized by their high dependence on temperature. After the reaction the Pd primary crystallites can be present in agglomerated form distributed over the entire support grain. The primary crystallites have furthermore grown to approx. 10 nm, compared with the Pd crystallites of the fresh catalyst (see FIG. 2, FIG. 3 and FIG. 4).

The catalysts can be characterized in that during the catalytic reaction Pd is detached and is redeposited on the support during and after the reaction. This can be demonstrated by suitable sampling during the reaction and Pd determinations. The detachment (min. 60° C.) and deposition (min. 120° C.) are characterized by their high dependence on temperature. The catalysts can be characterized in that after the reaction the Pd primary crystallites are present in agglomerated form distributed over the entire support grain. The primary crystallites have furthermore grown to approx. 10 nm, compared with the Pd crystallites of the fresh catalyst (see FIG. 2, FIG. 3 and FIG. 4).

The supported palladium catalyst can be employed in the process according to the invention with a content of 0.01 to 10 mol % Pd, preferably 0.1 to 5 mol % Pd, particularly preferably 0.1 to 1 mol % Pd, based on the coupling component employed in a deficit.

Substrates which can be employed in the processes according to the invention are the substrates according to the formulae I to IV.

Possible radicals for X in (I) as substituted aromatics are: Cl, Br, I, OTf, $N_2^+$, COCl, COOCOR, where R is, for example, alkyl($C_1$–$C_{12}$), aryl, preferably Br, I, OTf, $N_2^+$.

$R^1$–$R^5$ in (I) independently of one another can denote hydrogen, alkyl($C_1$–$C_{12}$), aryl, such as, for example, phenyl, naphthyl, F, Cl, Br, I, CN, $CF_3$, CHO, COalkyl ($C_1$–$C_8$), COOH, $NH_2$, NHalkyl($C_1$–$C_8$), N(alkyl($C_1$–$C_8$))$_2$, $NO_2$, NO, COOalkyl($C_1$–$C_8$), CONHalkyl($C_1$–$C_8$), OH, Oalkyl ($C_1$–$C_8$), Oaryl, OCOalkyl($C_1$–$C_8$), OCOphenyl, alkenyl, alkinyl, Si(alkyl($C_1$–$C_5$))$_3$. $R^5$ and $R^4$ or $R^4$ and $R^3$ or $R^3$ and $R^2$ or $R^2$ and $R^1$ can also be part of a fused aromatic or non-aromatic system. Possible radicals $R^1$ to $R^5$ are, for example, methyl, ethyl, n-propyl, isopropyl, n-butyl, i-butyl, tert-butyl, n-pentyl, i-pentyl, n-hexyl, n-heptyl, n-octyl, 2-ethylhexyl, 2-ethyldecyl, n-decyl, n-dodecyl, and furthermore methoxy, ethoxy, propoxy, isopropoxy, butoxy, pentyloxy, hexyloxy, octyloxy, 2-ethylhexyloxy, decyloxy, dodecyloxy, and furthermore carboxylic acid, carboxylic acid methyl ester, carboxylic acid ethyl ester, carboxylic acid propyl ester, carboxylic acid butyl ester, carboxylic acid pentyl ester, carboxylic acid hexyl ester, carboxylic acid 2-ethylhexyl ester, carboxylic acid phenyl ester, formyl, carboxylic acid amide, carboxylic acid dimethylamide, carboxylic acid diethylamide, carboxylic acid methylamide, and furthermore N,N-dimethylamino, N,N-diethylamino, N-methylamino, N-ethylamino, N,N-methylethylamino, N,N-dipropylamino, N,N-dibutylamino, N-morpholino, acetoxy, propionyloxy and butyryloxy groups.

Possible radicals for X in (II) as substituted olefins are: Cl, Br, I, OTf, OAc.

$R^6$ to $R^8$ in (II) independently of one another can denote hydrogen, alkyl($C_1$–$C_{12}$), aryl, such as, for example, phenyl, naphthyl, F, Cl, CN, $CF_3$, CHO, COalkyl($C_1$–$C_8$), COOH, $NO_2$, NO, COOalkyl($C_1$–$C_8$), COOphenyl, CONHalkyl ($C_1$–$C_8$), Oalkyl($C_1$–$C_8$), Oaryl, OCOalkyl($C_1$–$C_8$), OCOphenyl, alkenyl, alkinyl.

$R^9$ to $R^{11}$ in (III) independently of one another can denote hydrogen, alkyl($C_1$–$C_{12}$), aryl, such as, for example, phenyl, naphthyl, F, Cl, CN, $CF_3$, CHO, COalkyl($C_1$–$C_8$), COOH, $NO_2$, NO, COOalkyl($C_1$–$C_8$), COOphenyl, CONHalkyl ($C_1$–$C_8$), Oalkyl($C_1$–$C_8$), Oaryl, OCOalkyl($C_1$–$C_8$), OCOphenyl, alkenyl, alkinyl.

Possible radicals for X in (IV) as arylboron acids are: OM, where M is a monovalent cation, such as Li, Na, K or OH.

$R^{12}$ to $R^{16}$ in (IV) independently of one another can denote hydrogen, alkyl($C_1$–$C_{12}$), aryl, such as, for example, phenyl, naphthyl, F, Cl, Br, I, CN, $CF_3$, CHO, COalkyl ($C_1$–$C_8$), COOH, $NH_2$, NHalkyl($C_1$–$C_8$), N(alkyl($C_1$–$C_8$))$_2$, $NO_2$, NO, COOalkyl($C_1$–$C_8$), CONHalkyl($C_1$–$C_8$), OH, Oalkyl($C_1$–$C_8$), Oaryl, OCOalkyl($C_1$–$C_8$), OCOphenyl, alkenyl, alkinyl, Si(alkyl($C_1$–$C_5$))$_3$. $R^{16}$ and $R^{15}$ or $R^{15}$ and $R^{14}$ or $R^{14}$ and $R^{13}$ or $R^{13}$ and $R^{12}$ can also be part of a fused aromatic or non-aromatic system.

Possible radicals $R^1$ to $R^5$ are, for example, methyl, ethyl, n-propyl, isopropyl, n-butyl, i-butyl, tert-butyl, n-pentyl, i-pentyl, n-hexyl, n-heptyl, n-octyl, 2-ethylhexyl, 2-ethyldecyl, n-decyl, n-dodecyl, and furthermore methoxy, ethoxy, propoxy, isopropoxy, butoxy, pentyloxy, hexyloxy, octyloxy, 2-ethylhexyloxy, decyloxy, dodecyloxy, and furthermore carboxylic acid, carboxylic acid methyl ester, carboxylic acid ethyl ester, carboxylic acid propyl ester, carboxylic acid butyl ester, carboxylic acid pentyl ester, carboxylic acid hexyl ester, carboxylic acid 2-ethylhexyl ester, carboxylic acid phenyl ester, formyl, carboxylic acid amide, carboxylic acid dimethylamide, carboxylic acid diethylamide, carboxylic acid methylamide, and furthermore N,N-dimethylamino, N,N-diethylamino, N-methylamino, N-ethylamino, N,N-methylethylamino, N,N-dipropylamino, N,N-dibutylamino, N-morpholino, acetoxy, propionyloxy and butyryloxy groups.

Solvents which can be employed are in general aprotic and protic organic solvents, with the exception of carboxylic acids, and water and mixtures thereof, particularly preferably two-phase mixtures of an organic solvent and water.

Suitable solvents are, for example, optionally dimethylacetamide (DMAc), dimethylformamide (DMF), N-methylpyrrolidone (NMP), tetrahydrofuran (THF), toluene, dimethylsulfoxide (DMSO), water or isopropanol.

If an immiscible solvent mixture of organic solvent and water (two-phase mixture) is used, the catalyst can be exclusively in the phase most similar to the polarity of the support surface, and the salts which have participated in the reaction or are formed during the reaction can be in the aqueous phase.

If a single-phase solvent mixture is used, the reactants and the catalyst are dissolved or suspended in a solvent or miscible solvent mixture. If a two-phase solvent mixture is used, the catalyst, according to the polarity of the support surface, is in the phase most similar to the polarity of the support surface. If two immiscible solvents are used, all or some of the reactants and the catalyst can be present in various phases. If, for example, a solvent mixture of toluene/water is used, the catalyst is exclusively in the toluene phase, while the salts which have participated in the reaction or are formed during the reaction are in the aqueous phase. This can optionally be used for separating off the catalyst. If an immiscible solvent mixture is used, the phase containing the catalyst can simply be separated off by decanting. The organic solvent or solvent mixture is expediently added in 0.1 to 500 times, particularly preferably in 1 to 100 times the amount by weight, based on the substituted aromatic (I) employed or the substituted olefin (II) or the boron acid derivative (III).

Bases which are preferably used in the process according to the invention are alkali metal and alkaline earth metal hydroxides, such as LiOH, NaOH, KOH, RbOH, CsOH, $Mg(OH)_2$, $Ca(OH)_2$ or $Sr(OH)_2$, alkali metal and alkaline earth metal carbonates, such as $Li_2CO_3$, $Na_2CO_3$, $K_2CO_3$, $Rb_2CO_3$, $Cs_2CO_3$, $MgCO_3$, $CaCO_3$ or $SrCO_3$, alkali metal bicarbonates, such as $LiHCO_3$, $NaHCO_3$, $KHCO_3$ $RbHCO_3$ or $CsHCO_3$, alkali metal and alkaline earth metal acetates, such as LiOAc, NaOAc, KOAc, RbOAc, CsOAc, $Mg(OAc)_2$ or $Ca(OAc)_2$, alkali metal and alkaline earth metal formates, such as LiHCOO, NaHCOO, KHCOO, RbHCOO, CsHCOO, $Mg(HCOO)_2$, $Ca(HCOO)_2$ or $Sr(HCOO)_2$, alkali metal and alkaline earth metal alcoholates, such as, for example, LiOtBu, NaOtBu, KOtBu, RbOtBu, LiOiBu, NaOiBu, KOiBu, RbOiBu, LiOEt, NaOEt, KOEt, RbOEt, LiOMe, NaOMe, KOMe or RbOMe, primary, secondary and tertiary amines, such as, for example, triethylamine, ethyldiisopropylamine, tri-n-butylamine, and mixtures of two and more bases from the same group or the various groups.

The base can be employed in the process according to the invention in a proportion of 100–500 mol %, based on compounds according to the formulae (I), (II) or (IV).

The process according to the invention can be carried out at temperatures of between 60 and 220° C., preferably between 100 and 180° C., particularly preferably between 120 and 160° C. (Heck reaction) or at temperatures of between 40 and 180° C., preferably between 60 and 140° C., particularly preferably between 80 and 100° C. (Suzuki reaction).

The pressure under which the process according to the invention is carried out is only relevant in the case of gaseous educts. Atmospheric pressure is preferred here, and in the case of gaseous educts the pressure applied is not critical.

For carrying out the reaction in the sense of the process according to the invention, the heterogeneous palladium catalyst is suspended in the reaction mixture comprising educts, solvent or solvent mixture and base or base mixture. The reaction can be carried out here, but does not have to be, under inert gas conditions (for example nitrogen atmosphere). The solvents used can, but do not have to, be employed in a dried state. Non-dried solvents are preferred.

During the reaction, a detachment, characteristic of the base used, of the Pd introduced from the support and deposition of the Pd detached from the support on to the support occurs. The decisive parameters for the deposition of the Pd on the support are conversion, temperature, substrate, base and solvent. In this procedure, towards and after complete conversion above 110° C. in the case of electron-rich aromatics, reducing bases (amines or formates) and nonpolar solvents, in particular in two-phase solvent mixtures of an organic solvent and water, the deposition is particularly good and can be significantly below 5,000 ppm.

The content of the Pd remaining in the mother liquor after the reaction can thus be less than 5,000 ppm (based on the amount of Pd initially introduced), preferably less than 2,500 ppm, particularly preferably less than 500 ppm.

With the process according to the invention it is possible, surprisingly, to be able to achieve activities hitherto unknown for heterogeneous systems. Direct comparison with a known homogeneous catalyst system shows the same activity as is found for the process according to the invention. (Table 10 (Heck reaction), table 12 (Suzuki reaction)). No catalyst systems of such high activity for the substrates reacted here are found in the literature. It is moreover particularly surprising that ligands do not have to be added to the heterogeneous catalyst, as described in DE 4236103 A1, in order to achieve a high activity. It is even the case that ligands, such as, for example, triphenylphosphane, mean disadvantages in respect of activity and separating off of the catalyst.

Shmidt (A. F. Shmidt, L. V. Mavetova, *Kin. Catal.* 1996, 37, 406–408.) describes a detachment of the Pd of between 14 and 46% for iodoaromatics. Eisenstadt (A. Eisenstadt, Y. Keren, (IMI/TAMI Institute for Research & Development Ltd., EP 0 509 426 A2) finds only 86.5% Pd in the worked-up Pd/C catalyst. Arai (F. Zhao, M. Shirai, M. Arai, *J. Mol. Catal. A Chem.* 2000, 154, 39–44.) also investigates the course of the detachment of Pd with respect to time, but finds no substantial deposition on the support and concludes from this the lack of usability of the Pd/C catalysts for this reaction. For Suzuki reactions, no systematic investigations of the detachment of Pd have yet been carried out in the literature. The process according to the invention is furthermore particularly surprising in that the redeposition of the Pd which has dissolved achieves high values which were hitherto unknown, and by far exceeds that described in the literature.

MODES FOR CARRYING OUT THE INVENTION

Finally, the process according to the invention is particularly surprising in that no dehalogenation products are found. This applies both to the Heck and to the Suzuki reaction. Arai (F. Zhao, B. M. Bhanage, M. Shirai, M. Arai, *Chem. Eur. J.* 2000, 6, No. 5, 843–848.) reports that for bromoaromatics the main product is the dehalogenated bromoaromatic.

EXAMPLES

Preparation of the Catalyst

The catalysts are prepared by the processes familiar to the expert, by suspending a suitable support material in water, impregnating it with a suitable noble metal compound and fixing the noble metal to the support by using a suitable base. A reduction step can optionally follow. Pearlman (W. M. Pearlman, *Tetrahedron Lett.* 1967, 17, 1663–1664) is a literature reference known to the expert for the preparation of pulverulent noble metal catalysts. Catalysts are moreover to be obtained, for example, from Degussa-Hüls AG under the product names listed in table 1. The limitation to the six named catalysts from table 1 does not mean a restriction in respect of the effectiveness of other Degussa-Hüls Pd/C catalysts for the process according to the invention.

TABLE 1

Examples of suitable commercial Degussa-Hüls catalysts

| No. | Catalyst |
|---|---|
| 1 | E 105 NN/W 5% Pd |
| 2 | E 105 R/W 5% Pd |
| 3 | E 105 O/W 5% Pd |
| 4 | E 105 RO/W 5% Pd |
| 5 | E 105 KR/W 5% Pd |
| 6 | E 105 Y/W 5% Pd |

General Working Instructions 1 (Heck Reaction)

Explanation: The data of the Pd leaching values relate to the content of Pd in ppm in the mother liquor after the reaction and removal of the catalyst by filtration. The data in ppm relate to the amount of Pd introduced at the start of the reaction, i.e. 10,000 ppm Pd correspond to a Pd detachment of 1% (99% still on the support).

The catalyst code contains the letters W and D, which stand for moist (W) (water content of approx. 45–55%) or dry (D) (water content of approx. 2%).

10 mmol of substituted aromatic (I) or 10 mmol of substituted olefin (II), 12 mmol of base, 500 mg diethylene glycol dibutyl ether as an internal standard and the desired amount of the particular catalyst are weighed in a pressure tube. The solids are suspended or dissolved in 10 ml of solvent, the solvent being metered in by means of an Eppendorf pipette (10 ml). 12 mmol of olefin (III) are added, and after degassing for 5 min with argon (purity 4.6) (optional step) the closed pressure tube is introduced into an oil bath preheated to the reaction temperature. When the reaction has taken place (monitoring by GC), 1 ml of the reaction solution is removed and extracted in a test tube with in each case 1.5 ml of water and methylene chloride. The organic phase is dried over magnesium sulfate and analysed with the aid of GC. The remainder of the reaction solution is filtered, and a 5 ml sample is taken from the filtrate and evaporated in a rolled-edge glass. The residue is broken down with aqua regia at 80° C. until the entire residue has dissolved. The solution is analysed for Pd with the aid of ICP-OES or ICP-MS.

General Working Instructions 2 (Suzuki Reaction)

10 mmol of phenylboron acid derivative (IV), 12 mmol of substituted aromatic (I), 12 mmol of base, 500 mg diethylene glycol dibutyl ether as an internal standard and the desired amount of the particular catalyst are weighed in a pressure tube. The solids are dissolved or suspended in 10 ml of solvent, the solvent being metered in by means of an Eppendorf pipette (10 ml). After degassing for 5 min with argon (purity 4.6) (optional step) the closed pressure tube is introduced into an oil bath preheated to the reaction tem-

TABLE 2

Characterization of the catalysts.

| Catalyst[1] | Noble metal loading [wt. %] | Penetration depth [nm] | Crystallite size min. [nm] | Crystallite size max. [nm] | m[2] | $d_{50}$[3] | Dispersion [%] | CO chemisorption [ml/g] |
|---|---|---|---|---|---|---|---|---|
| E 105 NN/W 5% Pd | 5 | 50–300 | 1.00 | 18.25 | 4.79 | 2.36 | 23 | 2.89 |
| E 105 R/W 5% Pd | 5 | 50–300 | 1.72 | 18.24 | 4.07 | 2.84 | 27 | 2.50 |
| E 105 O/W 5% Pd | 5 | >300 | 1.36 | 12.00 | 3.07 | 2.34 | 36 | 1.97 |
| E 105 RO/W 5% Pd | 5 | 50–300 | 1.00 | 16.41 | 5.04 | 4.22 | 22 | 2.14 |
| E 105 KR/W 5% Pd | 5 | >300 | 1.36 | 12.74 | 3.96 | 3.48 | 28 | 2.90 |
| E 105 Y/W 5% Pd | 5 | >300 | 1.36 | 18.24 | 4.44 | 2.71 | 25 | 2.11 |

[1]Values for D types identical to those of w types; [2]arithmetic mean of the crystallite size; [3]median value.

Used Catalyst

Figure 1:
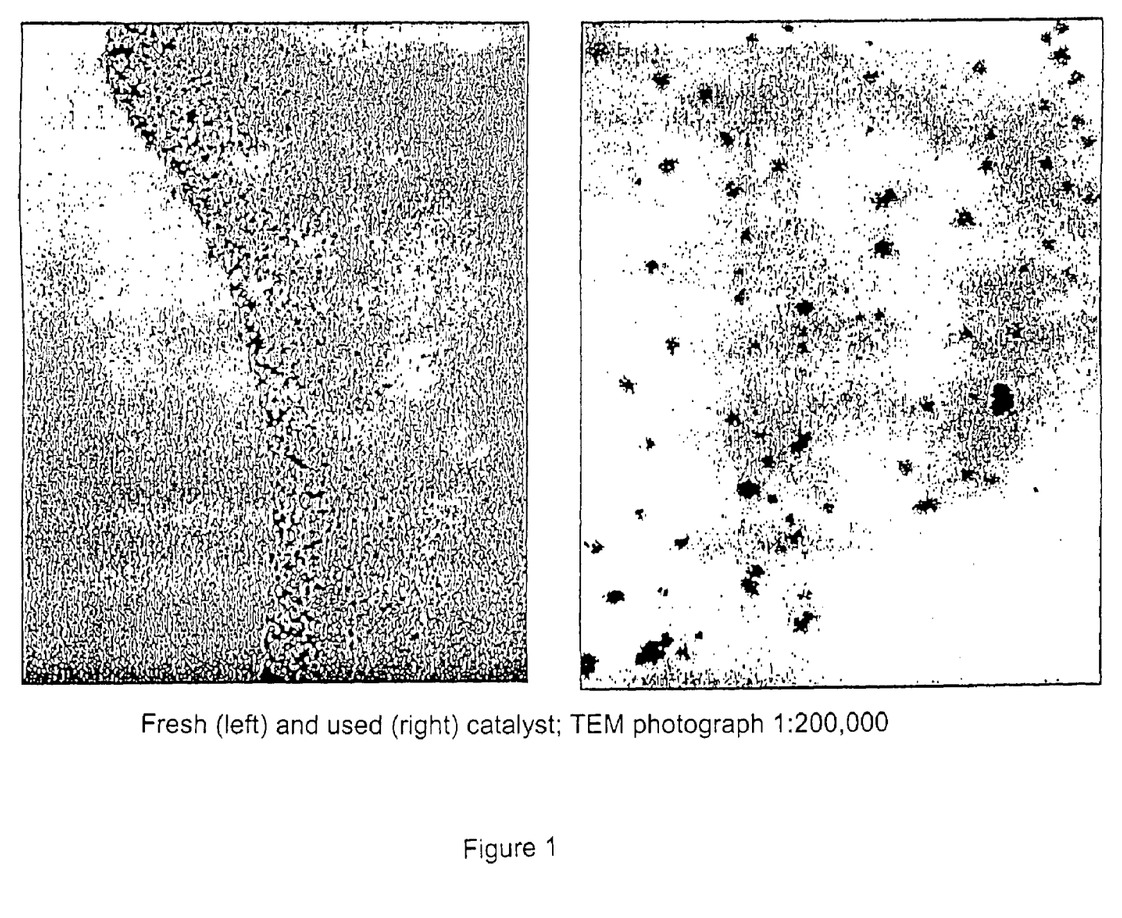
FIG. 1 shows a TEM photograph (1:200,000) of fresh (left) and used (right) catalyst.
Figure 2:
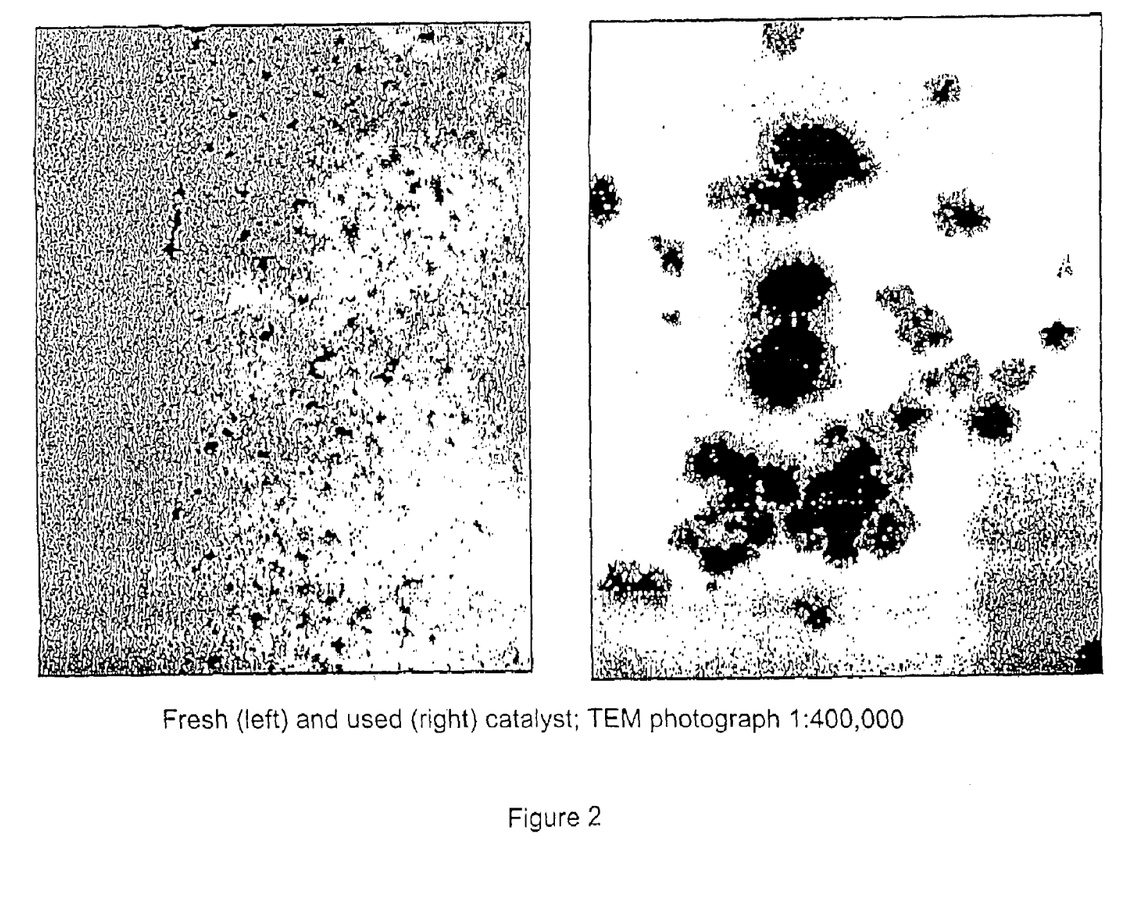
FIG. 2 shows a TEM photograph (1:400,000) of fresh (left) and used (right) catalyst.

Both the fresh and the used catalysts can be analysed, for example, with the aid of TEM. FIG. 1 and FIG. 2 show the fresh and used catalyst E 105 O/W 5% Pd.

Figure 3:
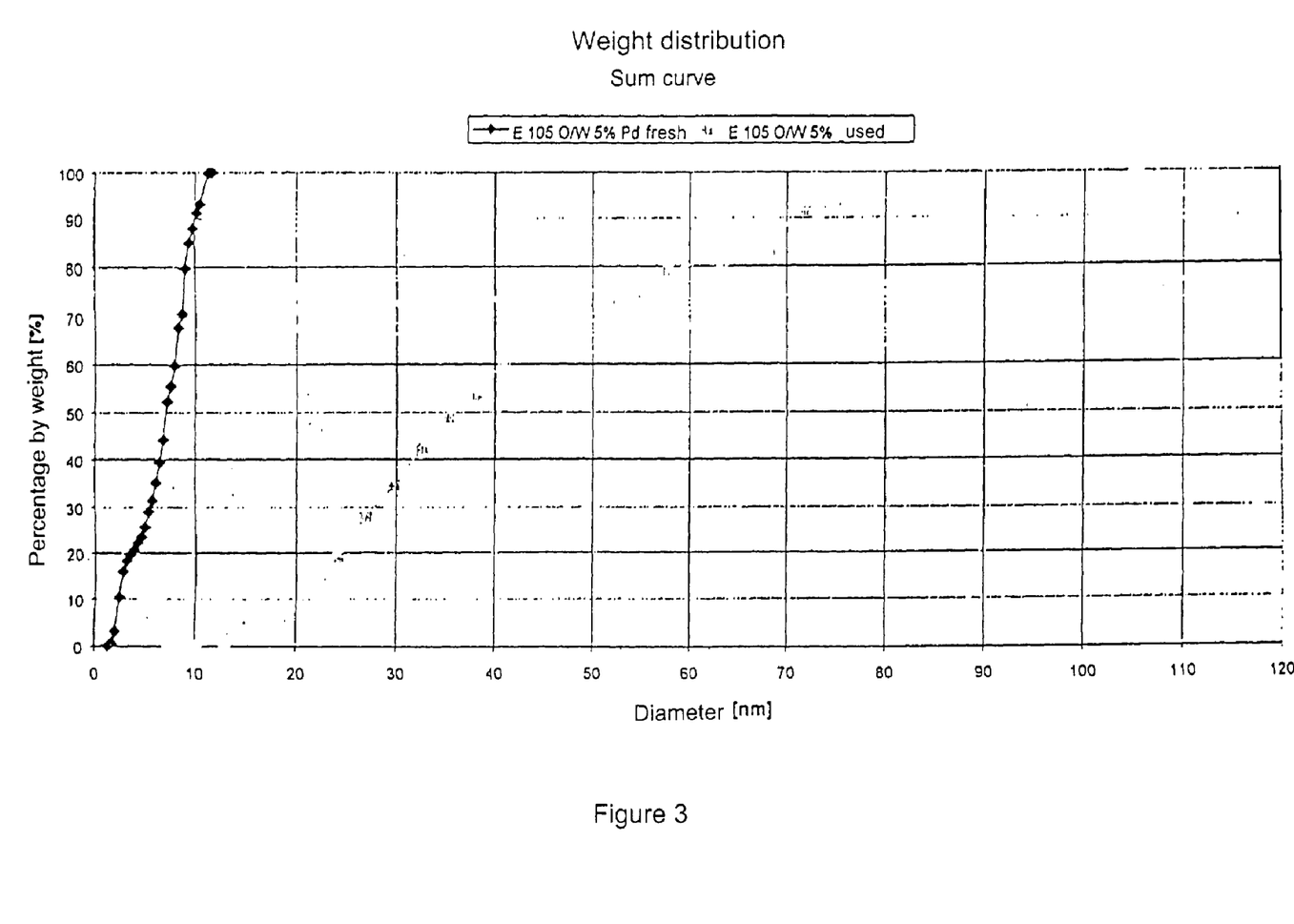
FIG. 3 shows a "percentage by weight (%)—diameter (nm)" plot of fresh and used E105 O/W 5% Pd catalyst.
Figure 4:
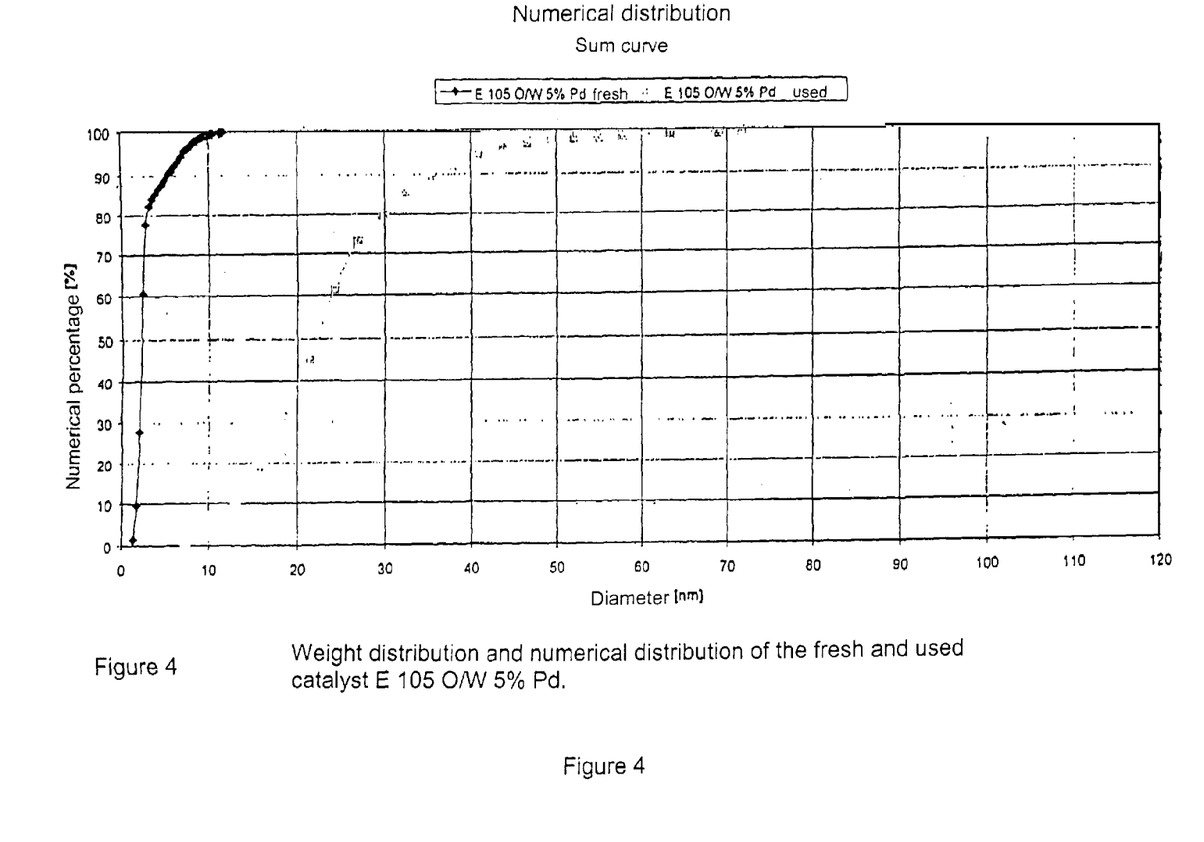
FIG. 4 shows a "numerical percentage (%)—diameter (nm)" plot of fresh and used E105 O/W 5% Pd catalyst.

The particle size growth can also be quantified by optical evaluation methods (see FIGS. 3 and 4).

perature. When the reaction has taken place (monitoring by GC), 1 ml of the reaction solution is removed and extracted in a test tube with in each case 1.5 ml of water and methylene chloride. The organic phase is dried over magnesium sulfate and analysed with the aid of GC. The remainder of the reaction solution is filtered, and a 5 ml sample is taken from the filtrate and evaporated in a rolled-edge glass. The residue is broken down with aqua regia at 80° C. until the entire residue has dissolved. The solution is analysed for Pd with the aid of ICP-OES or ICP-MS.

Examples 1–12

Examples 1–12 are carried out in accordance with general working instructions 1. The catalysts and substrates employed are those listed in table 3. The conditions can also be seen from table 3. The data show the influence of various catalysts on the yield and selectivity.

TABLE 3

Heterogeneous catalysts in the Heck reaction.[a]

| No. | Catalyst | Substrate | Amount of cat. [mol %] | Solvent | T [° C.] | t [h] | Base | Conversion [%] | E-Stilbene [%] | Z-Stilbene [%] | 1,1-disubst. [%] | Benzene [%] |
|---|---|---|---|---|---|---|---|---|---|---|---|---|
| 1 | E 105 NN/W 5% Pd | bromobenzene | 1 | DMAc | 140 | 2 | NaOAc | 95 | 87 | 0.7 | 7 | 0 |
| 2 | E 105 R/W 5% Pd | bromobenzene | 1 | DMAc | 140 | 2 | NaOAc | 60 | 55 | 0.5 | 4 | 0 |
| 3 | E 105 O/W 5% Pd | bromobenzene | 1 | DMAc | 140 | 2 | NaOAc | 90 | 81 | 0.7 | 7 | 0 |
| 4 | E 105 RO/W 5% Pd | bromobenzene | 1 | DMAc | 140 | 2 | NaOAc | 84 | 75 | 0.7 | 6 | 0 |
| 5 | E 105 KR/W 5% Pd | bromobenzene | 1 | DMAc | 140 | 2 | NaOAc | 79 | 69 | 0.6 | 6 | 0 |
| 6 | E 105 Y/W 5% Pd | bromobenzene | 1 | DMAc | 140 | 2 | NaOAc | 78 | 67 | 0.6 | 6 | 0 |
| 7 | E 105 KR/D 5% Pd | 4-bromoacetaphenone | 0.1 | DMAc | 80 | 1 | NaOAc | 80 | 75 | 0 | 2.4 | 0 |
| 8 | E 105 O/W 5% Pd | 4-bromoacetophenone | 0.1 | DMAc | 80 | 1 | NaOAc | 100 | 94 | 0 | 3.2 | 0 |
| 9 | E 105 RO/W 5% Pd | 4-bromoacetaphenone | 0.1 | DMAc | 80 | 1 | NaOAc | 85 | 78 | 0 | 2.7 | 0 |
| 10 | E 105 KR/D 5% Pd | 4-bromoacetaphenone | 0.1 | DMAc | 100 | 1 | NaOAc | 100 | 92 | 0 | 4 | 0 |
| 11 | E 105 O/W 5% Pd | 4-bromoacetaphenone | 0.1 | DMAc | 100 | 1 | NaOAc | 100 | 95 | 0 | 3 | 0 |
| 12 | E 105 RO/W 5% Pd | 4-bromoacetaphenone | 0.1 | DMAc | 100 | 1 | NaOAc | 100 | 91 | 0 | 2 | 0 |
| 13 | E 105 O/W 5% Pd | bromobenzene | 0.01 | NMP | 140 | 2 | NaOAc | 100 | 93 | 0.5 | 4 | 0 |

[a]Polymerized styrene, which is not recorded in the GC, occurs as a by-product in some cases.

Examples 14–15

Examples 14–15 are carried out according to general working instructions 1. The catalysts listed in table 4 are employed as the catalysts. The data show the influence of the water content.

TABLE 4

Dry and moist catalysts

| No. | Catalyst | Conversion [%] | Pd leaching [ppm] |
|---|---|---|---|
| 14 | E 105 O/W 5% Pd | 94 | 3,000 |
| 15 | E 105 O/D 5% Pd | 43 | 3,000 |

Conditions: Bromobenzene, DMAc, NaOAc, 140° C., 4 h, 1 mol % Pd

Examples 16–27

Examples 16–27 are carried out according to general working instructions 1. The catalysts listed in table 5 are employed as the catalysts and the reactions are carried out at the stated temperatures. The data show the influence of the temperature on the conversion and leaching.

TABLE 5

Influence of temperature on leaching

| No. | Catalyst | Temperature [° C.] | Conversion [%] | Pd leaching [ppm] |
|---|---|---|---|---|
| 16 | E 105 O/W 5% Pd | 60 | 8 | 12,000 |
| 17 | E 105 O/W 5% Pd | 80 | 100 | 310,000 |
| 18 | E 105 O/W 5% Pd | 100 | 100 | 11,000 |
| 19 | E 105 O/W 5% Pd | 120 | 100 | 2,000 |
| 20 | E 105 RO/W 5% Pd | 60 | 8 | 13,000 |
| 21 | E 105 RO/W 5% Pd | 80 | 83 | 286,000 |
| 22 | E 105 RO/W 5% Pd | 100 | 100 | 50,000 |
| 23 | E 105 RO/W 5% Pd | 120 | 100 | 2,500 |
| 24 | E 105 KR/D 5% Pd | 60 | 8 | 11,000 |
| 25 | E 105 KR/D 5% Pd | 80 | 76 | 655,000 |
| 26 | E 105 KR/D 5% Pd | 100 | 100 | 97,000 |
| 27 | E 105 KR/D 5% Pd | 120 | 100 | 2,500 |

Conditions: 4-Bromoacetophenone, DMAc, NaOAc, 4 h, 0.1 mol % Pd

Examples 28–30

Examples 28–30 are carried out according to general working instructions 1. The catalysts listed in table 6 are employed as the catalysts. The data show the influence of the noble metal loading on the conversion and leaching.

TABLE 6

Influence of the noble metal loading

| No. | Catalyst | Conversion [%] | Pd leaching [ppm] |
|---|---|---|---|
| 28 | E 105 O/W 1% Pd | 41 | 3,000 |
| 29 | E 105 O/W 5% Pd | 94 | 3,000 |
| 30 | E 105 O/W 10% Pd | 92 | 3,000 |

Conditions: Bromobenzene, DMAc, NaOAc, 140° C., 4 h, 1 mol % Pd.

Examples 31–36

Examples 31–36 are carried out according to general working instructions 1. The catalysts listed in table 7 are employed as the catalysts and the reactions are carried out using the stated bases. The data show the influence of the base on the Pd leaching.

TABLE 7

Influence of the base on the Pd leaching

| No. | Catalyst | Base | Solvent | Pd leaching [ppm] |
|---|---|---|---|---|
| 31 | E 105 O/W 5% Pd | tributylamine | NMP | 1,500 |
| 32 | E 105 O/W 5% Pd | NaOAc | NMP | 2,000 |
| 33 | E 105 O/W 5% Pd | NaHCOO | DMAc | 5 |
| 34 | E 105 O/W 5% Pd | triethylamine | DMAc | 400 |
| 35 | E 105 O/W 5% Pd | NaHCOO/NaOAc (1:6) | DMAc | 800 |
| 36 | E 105 O/W 5% Pd | NaOAc/triethylamine | DMAc | 400 |

Conditions: Bromobenzene, 140° C., 2 h, 1 mol % Pd.

Examples 37–42

Examples 37–42 are carried out according to general working instructions 1, the catalysts listed in table 8 are employed as the catalysts, and the reactions are carried out with the stated solvent mixtures. The data show the influence of the three-phase reaction on the conversion and yield.

TABLE 8

Three-phase reaction.

| No. | Catalyst | Solvent | Conversion [%] | Yield [%] |
|---|---|---|---|---|
| 37 | E 105 O/W 5% Pd | toluene | 1 | n.a. |
| 38 | E 105 RO/W 5% Pd | toluene | 1 | n.a. |
| 39 | E 105 KR/D 5% Pd | toluene | 5 | n.a. |
| 40 | E 105 O/W 5% Pd | toluene/water (1:1) | 100 | 92 |
| 41 | E 105 RO/W 5% Pd | toluene/water (1:1) | 100 | 80 |
| 42 | E 105 KR/D 5% Pd | toluene/water (1:1) | 100 | 82 |

Conditions: 4-Bromoacetophenone, NaOAc, 120° C., 2 h, 0.1 mol % Pd

The catalyst is suspended completely in the toluene phase. The salt load is exclusively in the aqueous phase. The aqueous phase is separated off with the aid of a separating funnel. The catalyst is removed by filtration.

Comparison Examples 1–7

Comparison examples 1–7 are carried out according to general working instructions 1, but the catalysts listed in table 9 are employed in addition to the catalyst E 105 O/W 5% Pd according to the invention. The data show the influence of the conditioning on the conversion and leaching.

TABLE 9

Conditioned catalysts

| No. | Catalyst | Conversion [%] | Pd leaching [ppm] |
|---|---|---|---|
| 1 | E 105 O/W 5% Pd | 94 | 3,000 |
| 2 | E 105 O/W 5% Pd 300° C., $N_2$ | 59 | 2,500 |
| 3 | E 105 O/W 5% Pd 500° C., $N_2$ | 14 | 2,500 |
| 4 | E 105 O/W 5% Pd 700° C., $N_2$ | 1 | 2,500 |
| 5 | E 105 O/W 5% Pd 700° C., $N_2 + H_2$ (95:5 vol) | 58 | 3,500 |
| 6 | E 105 O/W 5% Pd 300° C., $N_2 + H_2$ (95:5 vol) | 14 | 2,500 |

TABLE 9-continued

Conditioned catalysts

| No. | Catalyst | Conversion [%] | Pd leaching [ppm] |
|---|---|---|---|
| 7 | E 105 O/W 5% Pd 500° C., $N_2 + H_2$ (95:5 vol) | 5 | 4,500 |

Conditions: Bromobenzene, DMAc, NaOAc, 140° C., 4 h, 1 mol % Pd.

Comparison Example 7–10

The procedure is as described in general working instructions 1, but the catalysts listed in table 10 are employed instead of the heterogeneous catalysts according to the invention (for example E 105 O/W 5% Pd). The data show the equivalent nature of the heterogeneous system compared with the homogeneous, the advantage over the physical mixture of noble metal source and support, and the disadvantage of the use of ligands such as, for example, triphenylphosphane.

TABLE 10

Comparison with the homogeneous and other heterogeneous systems.

| No. | Catalyst | Conversion [%] | Yield (E-stilbene) [%] |
|---|---|---|---|
| 7 | E 105 O/W 5% Pd | 94 | 85 |
| 8 | Pd(OAc)$_2$[a]/TPP[b] (1:4) | 92 | 84 |
| 9 | E 105 O/W 5% Pd/TPP[b] | 62 | 55 |
| 10 | Pd(OAc)$_2$[a]/support of E 105 O/W 5% Pd | 15 | 6 |

Conditions: Bromobenzene, DMAc, NaOAc, 140° C., 3 h, 1 mol % Pd.
[a]22.5 mg; [b]TPP = triphenylphosphane, 105 mg.

Comparison Example 11–13

The procedure is as described in general working instructions 1, but various other catalysts are employed instead of the catalysts according to the invention. The data show the superiority of the process according to the invention and the Pd/C catalysts according to the invention.

TABLE 11

Other heterogeneous systems.

| No. | Catalyst | T [° C.] | t [h] | Conversion [%] | Yield (E-stilbene) [%] |
|---|---|---|---|---|---|
| 11 | Pd/MgO 1% | 140 | 20 | 50 | 45 |
| 12 | Pd/Al$_2$O$_3$ 5% | 140 | 20 | 44 | 38 |
| 13 | Pd/C 5%[a] | 140 | 20 | 60 | 50 |

[a]Aldrich 20568-0
Conditions: Bromobenzene, styrene, DMAc, NaOAc, 1 mol % Pd.

Examples 43–47

Examples 43–47 are carried out according to general working instructions 2. The catalysts and substrates listed in table 12 are employed as the catalysts and substrates. The conditions can also be seen from table 12. The data show the influence of various catalysts on the yield and selectivity.

TABLE 12

Heterogeneous catalysts in the Suzuki reaction.

| No. | Catalyst | Substrate | Amount of cat. [mol %] | Solvent | T [° C.] | t [h] | Base | Conversion [%] | Coupling product [%] | Benzene [%] |
|---|---|---|---|---|---|---|---|---|---|---|
| 43 | E 105 O/W 5% Pd | bromobenzene | 0.2 | NMP | 120 | 1 | NaOH | 35 | 35 | 0 |
| 44 | E 105 O/W 5% Pd | bromobenzene | 0.2 | DMAc | 120 | 1 | NaOH | 95 | 94 | 0 |
| 45 | E 105 O/W 5% Pd | bromobenzene | 0.2 | toluene | 120 | 1 | NaOH | 2 | 2 | 0 |
| 46 | E 105 O/W 5% Pd | bromobenzene | 0.2 | toluene/water (1:1) | 120 | 1 | NaOH | 95 | 95 | 0 |
| 47 | E 105 O/W 5% Pd | chlorobenzene | 1.0 | DMAc | 150 | 8 | NaOH | 75 | 60 | 10 |

The invention claimed is:

1. A process for carrying out CC coupling reactions comprising coupling substrates in a reaction solvent in the presence of a heterogeneous palladium catalyst, having a support, and a base under conditions suitable for the coupling reaction and palladium detachment into the reaction solvent and after the reaction is completed, separating off the Pd employed from the reaction solvent under conditions suitable for redeposition of the solvent Pd on the support, wherein the palladium catalyst is selected from those having a noble metal loading of 0.1 to 30% wt Pd, the catalyst support is selected from black carbon, active charcoal, wood charcoal or graphite and the substrate has one of the following formulas:

I

II

III

-continued

II

IV wherein 1) in formula I, X denotes Cl, Br, I, OTf, $N_2^+$, COCl, COOCOR, where R is alkyl($C_1$–$C_{12}$), or aryl, and $R^1$–$R^5$ denote hydrogen, alkyl($C_1$–$C_{12}$), aryl, F, Cl, Br, I, CN, $CF_3$, CHO, COalkyl($C_1$–$C_8$), COOH, $NH_2$, NHalkyl($C_1$–$C_8$), N(alkyl($C_1$–$C_8$))$_2$, $NO_2$, NO, COOalkyl($C_1$–$C_8$), CONHalkyl($C_1$–$C_8$), OH, Oalkyl ($C_1$–$C_8$), Oaryl, OCOalkyl($C_1$–$C_8$), OCOphenyl, alkenyl, alkynyl, Si(alkyl($C_1$–$C_8$))$_3$, wherein $R^5$ and $R^4$ or $R^4$ and $R^3$ or $R^3$ and $R^2$ or $R^2$ and $R^1$ can also be part of a fused aromatic or non-aromatic system, 2) in formula II, X denotes Cl, Br, I, OTf, OAc, and $R^6$ to $R^8$ in (II) denote hydrogen, alkyl($C_1$–$C_{12}$), aryl, F, Cl, CN, $CF_3$, CHO, COalkyl($C_1$–$C_8$), COOH, $NO_2$, NO, COOalkyl($C_1$–$C_8$), COOphenyl, CONHalkyl($C_1$–$C_8$), Oalkyl($C_1$–$C_8$), Oaryl, OCOalkyl($C_1$–$C_8$), OCOphenyl, alkenyl, alkynyl, 3) in formula III, $R^9$ $R^{11}$ denote hydrogen, alkyl($C_1$–$C_{12}$), aryl, F, Cl, CN, $CF_3$, CHO, COalkyl($C_1$–$C_8$), COOH, $NO_2$, NO, COOalkyl ($C_1$–$C_8$), COOphenyl, CONHalkyl($C_1$–$C_8$), Oalkyl ($C_1$–$C_8$), Oaryl, OCOalkyl($C_1$–$C_8$), OCOphenyl, alkenyl, alkynyl, and 4) in formula IV, X denotes OM, where M is a monovalent cation, and $R^{12}$ to $R^{16}$ denote hydrogen, alkyl($C_1$–$C_{12}$), aryl, F, Cl, Br, I, CN, $CF_3$, CHO, COalkyl($C_1$–$C_8$), COOH, $NH_2$, NHalkyl ($C_1$–$C_8$), N(alkyl($C_1$–$C_8$))$_2$, $NO_2$, NO, COOalkyl ($C_1$–$C_8$), CONHalkyl($C_1$–$C_8$), OH, Oalkyl($C_1$–$C_8$), Oaryl, OCOalkyl($C_1$–$C_8$), OCOphenyl, alkenyl, alkynyl, Si(alkyl($C_1$–$C_5$))$_3$, wherein $R^{16}$ and $R^{15}$ or $R^{15}$ and $R^{14}$ or $R^{14}$ and $R^{13}$ or $R^{13}$ and $R^{12}$ can also be part of a fused aromatic or non-aromatic system; and wherein the required base include alkali metal and alkaline earth metal hydroxides, alkali metal and alkaline earth metal carbonates, alkali metal bicarbonates, alkali

I metal and alkaline earth metal acetates, alkali metal and alkaline earth metal formates, alkali metal and alkaline earth metal alcoholates, primary, secondary and tertiary amines and mixtures thereof.

2. The process according to claim 1, wherein no ligands are present together with the catalyst.

3. The process according to claim 1, wherein the catalyst, after its preparation by wet chemistry, is not further treated in a separate conditioning step.

4. The process according to claim 1, wherein the catalyst has Pd crystallites with a penetration depth between 50 and 300 nm and with a homogeneous distribution.

5. The process according to claim 1, wherein the catalyst has a noble metal dispersion between 10 and 60%.

6. The process according to claim 1, wherein the catalysts have a low degree of reduction of between 0 and 50%.

7. The process according to claim 1, wherein the support material has a BET surface area of at least 800 $m^2/g$, a micropore volume of less than 0.4 ml/g, a mesopore volume of greater than 0.3 ml/g and a macropore volume of greater than 0.3 ml/g.

8. The process according to claim 1, wherein the reaction has a characteristic detachment of the Pd introduced from the support and during and after the reaction redeposition of the Pd detached from the support on to the support occurs.

9. The process according to claim 1, wherein the content of Pd remaining in the reaction solvent after the reaction is less than 5,000 ppm, based on the amount of Pd initially introduced.

10. The process according to claim 1, wherein the supported palladium catalyst has a content of 0.01 to 10 mol % Pd, based on the coupling component, which is employed in a deficit.

11. The process according to claim 1, wherein the reaction solvent includes aprotic and protic organic solvents, with the exeption of carboxylic acids, and water and mixtures thereof.

12. The process according to claim 1, wherein if the reaction solvent includes an immiscible solvent mixture of organic solvent and water (two-phase mixture), the catalyst is exclusively in the phase most similar to the polarity of the support surface, and the salts which have participated in the reaction or are formed during the reaction can be in the aqueous phase.

13. The process according to claim 1, wherein if the reaction solvent includes an immiscible solvent mixture, the phase containing the catalyst is simply separated off by decanting.

14. The process according to claim 1, wherein the reaction mixture is an organic solvent or solvent mixture is added in 0.1 to 500 times by weight based on the substituted aromatic (I) or the substituted olefin (II), (III) or the phenyl boron acid derivative (IV) employed.

15. The process according to claim 1, wherein the base is employed in a proportion of 100–500 mol %, based on (I), (II) or (IV).

16. The process according to claim 1, wherein the process is carried out at temperatures of between 60 and 220° C.

17. The process according to claim 1, wherein the pressure under which the process is carried out is atmospheric pressure.

18. The process according to claim 1, wherein the noble metal loading is 1 to 10 wt. %.

19. The process according to claim 18, wherein the noble metal loading is 5 wt. %.

20. The process according to claim 5, wherein the dispersion is between 15 and 50%.

21. The process according to claim 20, wherein the dispersion is between 20 and 40%.

22. The process according to claim 6, wherein the degree of reduction is between 0 and 40%.

23. The process according to claim 22, wherein the degree of reduction is-between 0 and 20%.

24. The process according to claim 9, wherein the content of Pd remaining in the reaction solvent is less than 2,500 ppm.

25. The process according to claim 9, wherein the content of Pd remaining in the reaction solvent is less than 500 ppm.

26. The process according to claim 10, wherein the content is 0.1 to 5 mol % Pd.

27. The process according to claim 26, wherein the content is 0.1 to 1 mol % Pd.

28. The process according to claim 11, wherein the water and mixtures thereof include two-phase mixtures of an organic solvent and water.

29. The process according to claim 14, wherein the organic solvent or solvent mixture is expediently added in 1 to 100 times the amount by weight, based on the substituted aromatic (I) employed or the substituted olefin (II) or the boron acid derivative (III).

30. The process according to claim 16, wherein the temperatures are between 100 and 180° C.

31. The process according to claim 30, wherein the temperatures are between 120 and 160° C.

32. The process according to claim 1, wherein the process is carried out at temperatures of between 40 and 180° C.

33. The process according to claim 32, wherein the temperature is between 60 and 140° C.

34. The process according to claim 33, wherein the temperature is between 80 and 100° C.

* * * * *